United States Patent
DiSilvestro

(10) Patent No.: US 9,211,297 B2
(45) Date of Patent: Dec. 15, 2015

(54) EXERCISE PERFORMANCE-INCREASING NUTRITIONAL SUPPLEMENT AND RELATED METHODS AND COMPOSITIONS

(71) Applicant: Ohio State Innovation Foundation, Columbus, OH (US)

(72) Inventor: Robert DiSilvestro, Columbus, OH (US)

(73) Assignee: Ohio State Innovation Foundation, Columbus, OH (US)

( * ) Notice: Subject to any disclaimer, the term of this patent is extended or adjusted under 35 U.S.C. 154(b) by 0 days.

(21) Appl. No.: 13/891,750

(22) Filed: May 10, 2013

(65) Prior Publication Data

US 2013/0302382 A1    Nov. 14, 2013

Related U.S. Application Data

(60) Provisional application No. 61/645,757, filed on May 11, 2012.

(51) Int. Cl.

| | | |
|---|---|---|
| *A61K 47/00* | (2006.01) |
| *A61K 31/685* | (2006.01) |
| *A61K 31/205* | (2006.01) |
| *A61K 31/315* | (2006.01) |
| *A61K 31/295* | (2006.01) |
| *A61K 31/30* | (2006.01) |
| *A23L 1/305* | (2006.01) |
| *A23L 1/304* | (2006.01) |
| *A61K 31/555* | (2006.01) |

(52) U.S. Cl.
CPC ............. *A61K 31/685* (2013.01); *A23L 1/3045* (2013.01); *A23L 1/3051* (2013.01); *A61K 31/205* (2013.01); *A61K 31/295* (2013.01); *A61K 31/30* (2013.01); *A61K 31/315* (2013.01); *A61K 31/555* (2013.01); *A23V 2002/00* (2013.01)

(58) Field of Classification Search
None
See application file for complete search history.

(56) References Cited

FOREIGN PATENT DOCUMENTS

CN    103598421 A    *    2/2014

* cited by examiner

*Primary Examiner* — Susan Tran
(74) *Attorney, Agent, or Firm* — Roger D. Emerson; Emerson, Thomson & Bennett, LLC

(57) ABSTRACT

The present invention provides a nutritional supplement, comprising L-carnitine and phosphatidylserine; and optionally, further comprises at least one mineral selected from the group consisting of: iron; copper and zinc; and optionally, further comprises ferrous glycinate, copper glycinate and zinc glycinate.

20 Claims, 4 Drawing Sheets
(4 of 4 Drawing Sheet(s) Filed in Color)

EXERCISE PERFORMANCE-INCREASING NUTRITIONAL SUPPLEMENT AND RELATED METHODS AND COMPOSITIONS

CROSS REFERENCE TO RELATED APPLICATIONS

This application claims the benefit of U.S. Provisional Application No. 61/645,757 filed May 11, 2012, the disclosure of which is incorporated herein by reference.

STATEMENT REGARDING FEDERALLY-SPONSORED RESEARCH

This invention was not made with U.S. Government financial support.

TECHNICAL FIELD OF THE INVENTION

The present invention relates to nutritional supplements. The technical field is therefore related to food and nutrition, including beverages. The field also includes sports and/or related endurance/exercise methods.

BACKGROUND OF THE INVENTION

Many food and vitamin supplement products tout a sports advantage angle, but rarely do they provide statistically-supported exercise-performance research to support the claims. Few have scientific research demonstrating that the exact product produces better performance of exercise. Very few have demonstrated a superior effect on aerobic exercise activities, especially the endurance sports. Traditional formulations are directed at ameliorating deficiencies, not increasing performance.

The present invention is based on the observation that certain formulations of various ingredients can improve aerobic exercise performance, with or without a measurable or pathological deficiency in the nutrient provided.

Women athletes who consumed the present formulation for five weeks decreased their three-mile run time by an average of about fifty seconds in fitness trained women. Similarly trained women who consumed a control formulation over the same period of time showed no statistically significant effect. Minor differences in training during the trial do not account for the speed increases in the test group.

SUMMARY OF THE INVENTION

The present invention provides a nutritional supplement, comprising L-carnitine and phosphatidylserine. Provided are those supplements which further comprise at least one mineral selected from the group consisting of: iron; copper and zinc. Also provided are supplements which comprise ferrous glycinate, copper glycinate and zinc glycinate.

The present invention provides nutritional supplements, comprising L-carnitine; phosphatidylserine; ferrous glycinate, copper as copper glycinate; and zinc as zinc glycinate.

Also provided are such nutritional supplements, comprising:
  0.5 g to 5 g L-carnitine; and
  300 mg to 1.5 g phosphatidylserine;
  10 mg to 75 mg iron as ferrous glycinate;
  0.5 mg to 3 mg copper as copper glycinate; and
  8 mg to 17 mg zinc as zinc glycinate,
wherein the supplement is apportioned amongst at least two doses.

Also provided are such nutritional supplements, comprising:
  0.5 g to 2.5 g L-carnitine tartrate;
  300 mg to 700 g to phosphatidylserine;
  25 mg to 50 mg iron as ferrous glycinate;
  1.5 mg to 2.5 mg copper as copper glycinate; and
  13 mg to 16 mg zinc as zinc glycinate
wherein the supplement is apportioned amongst at least two doses.

The present invention also provides multivitamin formulations, comprising:
  approximately 1 g L-carnitine tartrate;
  approximately 400 mg phosphatidylserine;
  approximately 36 mg iron as ferrous glycinate;
  approximately 2 mg copper as copper glycinate; and
  approximately 15 mg zinc as zinc glycinate,
wherein the formulation is apportioned amongst at least two doses.

Also provided are such nutritional supplements, wherein the supplement further comprises one or more composition selected from the group consisting of: protein; carbohydrate; fiber; fat; electrolyte; stimulant; vitamin; mineral; herb; polymer; water; artificial sweetener; artificial fat; and pharmoactive molecule.

Also provided are such nutritional supplements, which is optimized for use in a mammal selected from the group consisting of: mouse; rat; bovine; horse; swine; dog; cat; and human.

Also provided are such nutritional supplements, which are optimized for use in a female human.

Also provided are such nutritional supplements, wherein the supplement further comprises a form selected from the group consisting of: liquid; gel; solid; tablet; capsule; crystals; and powder.

Also provided are such nutritional supplements, wherein the supplement further comprises a form selected from the group consisting of: multivitamin; drink; bar; gel; powdered drink mix; concentrated liquid drink mix; gel drink mix; crystalline food.

Also provided are such nutritional supplements, wherein the supplement is a liquid selected from the group consisting of: water; orange juice; apple juice; grape juice; mixed juice; cranberry juice; pomegranate juice; cow's milk; goat's milk; sheep's milk; nut extract; soy extract; grain extract; carbonated beverage; alcoholic beverage; flavored beverage.

Also provided are such nutritional supplements, wherein the supplement is a food selected from the group consisting of: dairy product; ready-to-eat cereal; cookie; cake; cracker; pretzel; honey; and bar.

Also provided are such nutritional supplements, wherein one or more of the ingredients is formulated for a quality selected from the group consisting of: liquid dispersement resistance or enhancement; colloid formation resistance or enhancement; heat stability; powdering resistance or enhancement; dissolving resistance or enhancement; bulk formation or reduction; maillard reaction resistance or enhancement; bitterness resistance; flavor enhancement; appearance enhancement; processing enhancement; process expense reduction.

Also provided are such nutritional supplements, wherein the L-carnitine is L-carnitine tartrate.

Also provided are such nutritional supplements, wherein a mineral is in an encapsulated, micellar form.

The present invention also provides methods to increase exercise performance capacity in a human, comprising administering a nutritional supplement herein.

Also provided are such methods, wherein the human is a female human selected from the group consisting of: adult woman; and adolescent girl.

Also provided are such methods, wherein the human is a female human competitive athlete who trains for a sport selected from the group consisting of: cross-country running; soccer; softball;

Also provided are such methods, wherein the supplement is administered via 1-10 servings per day.

Also provided are such methods, wherein the supplement is administered via 4-8 servings per day.

Also provided are such methods, wherein the supplement is administered via 6 servings per day, three times a day, via capsule or tablet.

Also provided are such compositions or methods as described and shown herein.

DEFINITIONS

All terms herein have the meaning as understood in the global scientific art (in the case of a scientific term) and/or in general U.S. English usage (in the case of non-scientific terms).

Various objects and advantages of this invention will become apparent to those skilled in the art from the following detailed description, when read in light of the accompanying figures.

BRIEF DESCRIPTION OF THE FIGURES

The application contains one or more figures executed in color and/or one or more photographs. Copies of color figures(s) and/or photograph(s) will be provided upon request and payment of the necessary fee.

DETAILED DESCRIPTION OF THE INVENTION

Figure 1:
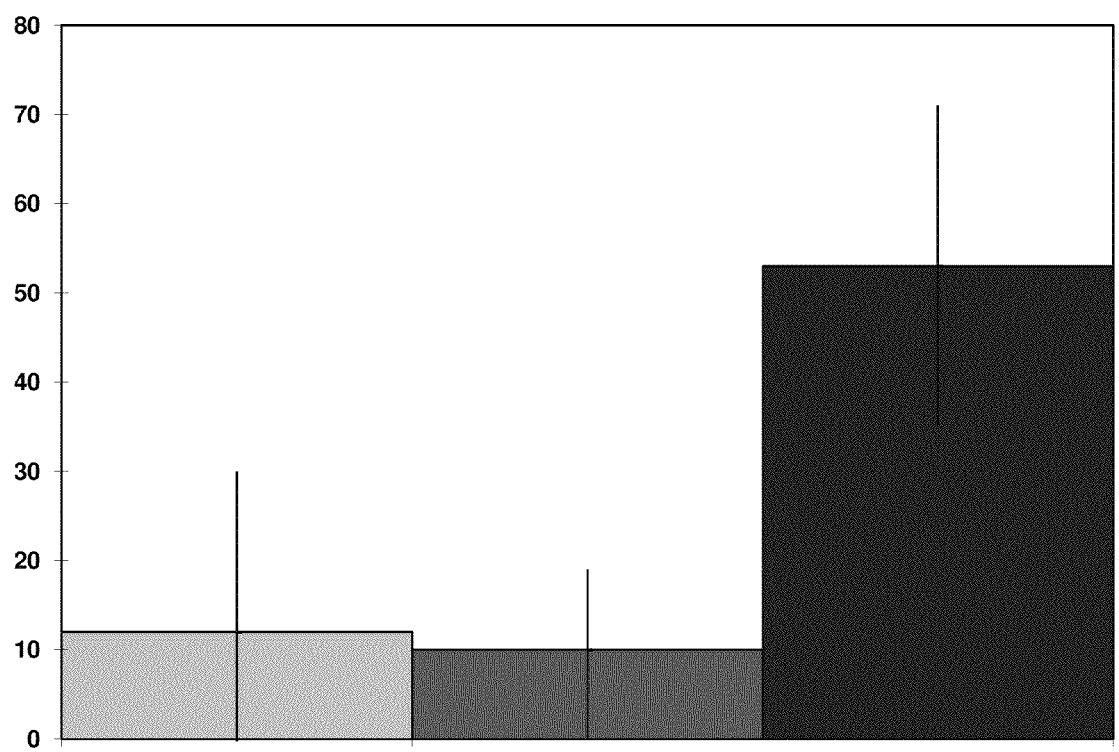
FIG. 1. The decrease in run time after nutritional intervention.

Herein, the inventors disclose that certain combinations of nutrients are able to increase exercise performance. In moderately aerobic running trained, young adult women, consumption of the four test ingredients for 5 weeks improved aerobic exercise performance in a statistically-significant manner. Performance was evaluated as time in a 5K run (performance in a familiar activity), distance covered in a 25 minute stationary bicycle activity (performance in an unfamiliar familiar activity), 90 second step test shortly after the run and bicycling (for short term muscle recovery).

The improvement with the four ingredients exceeded that of placebo or a combination of the four ingredients in different forms. The last group inclusion is motivated by the fact that the ingredients of this proposal are often given in forms that are cheaper, but less bioactive.

Carnitine is a compound naturally found in foods such as meat and is made in the body from lysine and methionine, but internal production does not always provide optimal body levels. L-carnitine is optionally obtained from Lonza Corporation, under the brand name L Carnipure®. In the present invention, carnitine is provided in optimal forms and amounts.

Phosphatidylserine may be consumed in the diet and is made in the body from serine, an amino acid obtained in the diet. In the present invention, phosphatidylserine is provided in optimal forms and amounts.

Ferrous bis-glycinate is optionally obtained from Albion Corporation, under the brand name Ferrochel®. In the present invention, ferrous bis-glycinate is provided in optimal forms and amounts.

Beef is the best source of zinc among commonly eaten foods. The zinc in most multi supplements is zinc oxide. Stand alone zinc supplements generally utilize zinc gluconate. Breakfast cereals, when fortified with zinc, generally use zinc oxide. In the present invention, zinc is provided in optimal forms and amounts.

The copper in most multi supplements is copper oxide. Stand alone copper supplements generally utilize copper gluconate. Food fortifications with copper are limited mostly to meal replacement products, which use mostly copper oxide. Breakfast cereals are not fortified with copper. In the present invention, copper is provided in optimal forms and amounts.

Preferred mineral complexes are the glycinate complexes, which may be optionally obtained from Albion Laboratories. The present invention does not cause problems with stomach upset, an issue with some copper or zinc complexes.

The present formulation influenced various measures of aerobic exercise performance. The present formulation having minerals in glycinate forms generally showed better results than the version with the traditional mineral complexes. While moderate iron deficiency seemed to occur in some of the subjects and was corrected after supplementation in some but not all of these subjects, exercise performance did not depend on correction of a deficiency. Zinc status, based on one measure, was improved to some extent by both non-placebo interventions.

Also provided are methods wherein the female human is selected from the group consisting of: fitness exerciser; competitive athlete; sporadic exerciser; and rehabilitation exerciser; fitness instructor; woman recovering from injury; woman recovering from illness; woman recovering from surgery; military personnel; law enforcement personnel; construction worker; health care provider; surgeon; emergency responder; and manual laborer.

Also provided are methods wherein the human is a female human who trains for a sport selected from the group consisting of: walking; running; track events; swimming; triathlon; bicycling; hockey; lacrosse; soccer; basketball; softball; golf; volleyball; squash; sailing; canoeing; kayaking; rowing; wheelchair racing; wrestling; boxing; football; diving; tennis; ice skating; inline skating; cheerleading; mountaineering; rockclimbing; skiing; snowboarding; surfing; martial arts; dance; gymnastics; ultimate Frisbee; backpacking; and marching band.

Also provided are methods wherein the human is a female human competitive athlete who trains for a sport selected from the group consisting of: cross-country running; soccer; softball; volleyball; basketball; golf; track; swimming; dance; cheerleading; and triathlon.

The present invention is further defined in the following Examples, in which all parts and percentages are by weight, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference. The following examples are intended to illustrate certain preferred embodiments of the invention and should not be interpreted to limit the scope of the invention as defined in the claims, unless so specified. Data are presented as Mean±SEM and compared using Student's t-test. Significance was accepted at $p<0.05$.

EXAMPLES

Certain embodiments of the present invention are defined in the Examples herein. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions. All publications, including patents and non-patent literature, referred to in this specification are expressly incorporated by reference herein. Citation of the any of the documents recited herein is not intended as an admission that any of the foregoing is pertinent prior art. All statements as to the date or representation as to the contents of these documents is based on the information available to the applicant and does not constitute any admission as to the correctness of the dates or contents of these documents.

Example 1

Aerobic exercise performance in response to three powdered ingredient mixes taken twice per day for 5 weeks.
Materials
Placebo: Cake Mix
Test Formula 1 (aka Traditional or New1):

| Ingredient (source) | Weight per day of active component (which is less than the weight of the formulated component) |
|---|---|
| L-carnitine tartrate (Lonza) | 2 g of L-carnitine (< wt of L-carnitine tartrate) |
| Phosphaytidylserine (Cheminutra) | 800 mg |
| Ferrous sulfate (Premium Ingredients International) | 36 mg iron (< wt of ferrous sulfate) |
| Copper gluconate (Premium Ingredients International) | 2 mg copper (< wt of copper gluconate) |
| Zinc gluconate (Premium Ingredients International) | 15 mg zinc (< wt of zinc gluconate) |

Test Formula 2 (aka Chelate or New2):

| Ingredient (source) | Weight per day (which is less than the weight of the formulated component) |
|---|---|
| L-carnitine tartrate (Lonza) | 2 grams of carnitine (< wt carnitine tartrate) |
| Phosphaytidylserine (Cheminutra) | 800 mg |
| Ferrous bis-glycinate (Albion) | 36 mg iron (< wt of ferrous bis-glycinate) |
| Copper glycinate (Albion) | 2 mg copper (< wt of copper glycinate) |
| Zinc glycinate (Albion) | 15 mg zinc (< wt of zinc glycinate) |

Methods

Three groups of fifteen women were formed. All women entered the study with previous aerobic exercise training. One group ingested placebo; one group received Test Formula I; and one group received Test Formula II. The powdered ingredient mixes were prepared and consumed as powders mixed by the subjects in any beverage they normally consumed or in water plus flavorings of their choice. Each woman ingested one of three types of powdered ingredient mixes twice per day for five weeks.

Each woman completed an aerobic exercise challenge before and after the 5 week nutritional intervention. The challenge consisted of three parts: a timed three mile run, distance covered after 25 minutes on a stationary bike, and a 90 second step test. A short walking period was done between each exercise phase.

Exercise Results

The three mile run time was significantly decreased by the new combination with the Albion minerals, but not by the other two treatments; the average decrease was a little under one minute:

|  | Placebo | Test Formula I | Test Formula II |
|---|---|---|---|
| Run-Pre | 26.6 ± 3.3 | 26.8 ± 3.5 | 26.5 ± 2.3 |
| Run-Post | 26.5 ± 3.3 | 26.4 ± 3.4 | 25.7 ± 2.4* |

Run times are means of minutes ± SD (decimals indicate portion of minutes, not seconds)
*p < 0.05 paired t-test For bike distance, both placebo and the new combination with the Albion minerals produced a statistically significant increase in mileage.

|  | Placebo | Test Formula I | Test Formula II |
|---|---|---|---|
| Bike-Pre | 6.2 ± 0.8 | 6.1 ± 1.1 | 6.0 ± 0.8 |
| Bike-Post | 6.5 ± 0.9* | 6.3 ± 1.1 | 6.5 ± 0.6* |

Bike distances are mile means ± SD
*p < 0.05, paired t-test

The average change for the bike distance was greater for the Test Formula II group versus the placebo, unpaired t-test (FIG. 1.)

For the step test, the Test Formula I treatment produced an increase that was barely significant by a one-tailed, paired t-test. The Test Formula II treatment produced an increase that was strongly significant by a two-tailed, paired t-test. I added underlines for emphasis.

|  | Placebo | Test Formula I | Test Formula II |
|---|---|---|---|
| Steps-Pre | 40.7 ± 7.0 | 41.0 ± 5.9 | 40.3 ± 6.4 |
| Steps-Post | 42.3 ± 6.4 | 44.1 ± 5.2* | 43.8 ± 4.8** |

Figure 2:
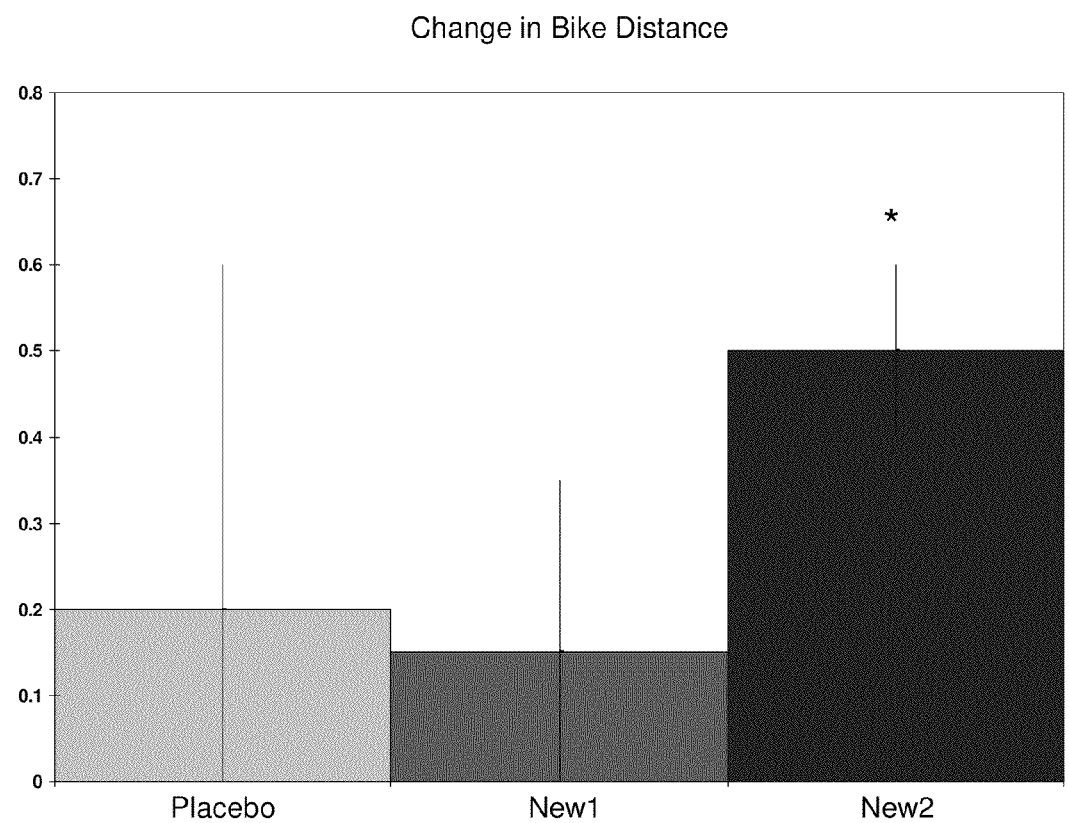
FIG. 2. The average change for the bike distance after nutritional intervention.

Steps are number of step up means ± SD
*p < 0.05 paired t-test, one tailed
**p < 0.005 paired t-test, two tailed The average change for the step test was greater for the both Test Formula groups versus placebo, but not versus each other. (FIG. 2). However, the effect was more consistent among subjects in the Test Formula II test.

Blood/Saliva Test Results for Pre-Exercise, Pre- and Post-Treatment

Figure 3:
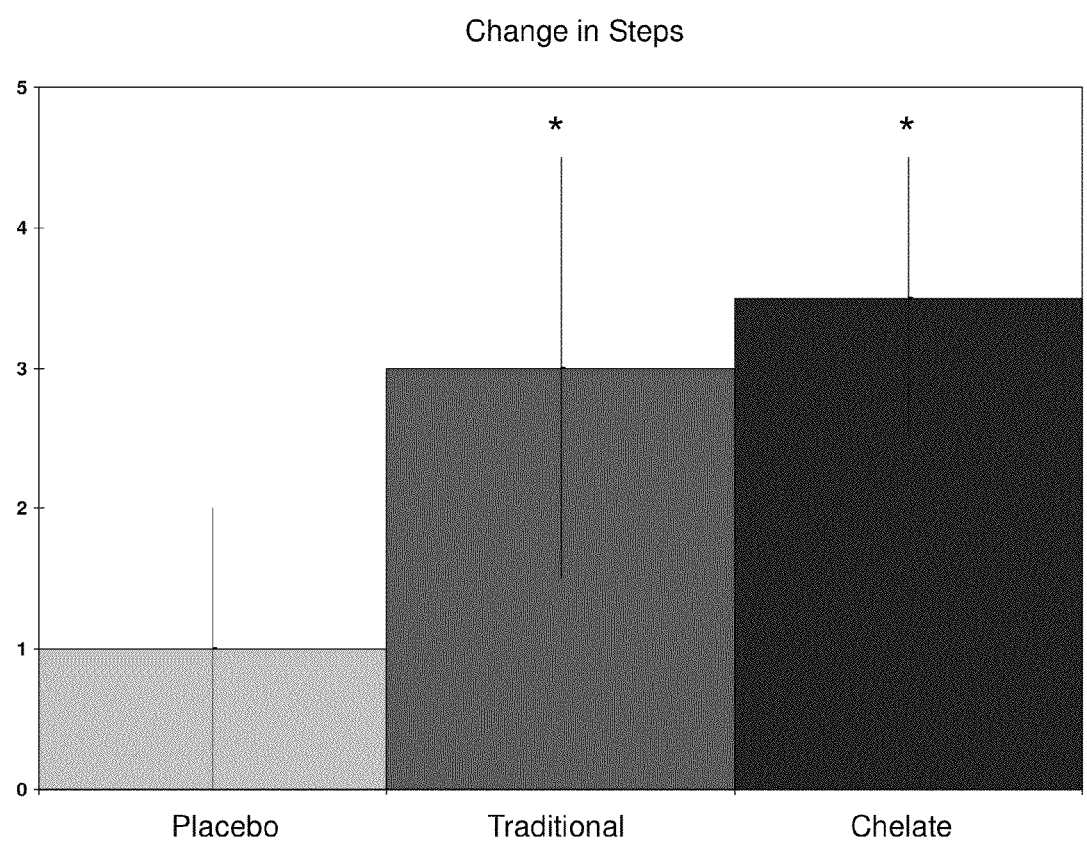
FIG. 3. The average change for steps in a fixed time after nutritional intervention.
Figure 4:
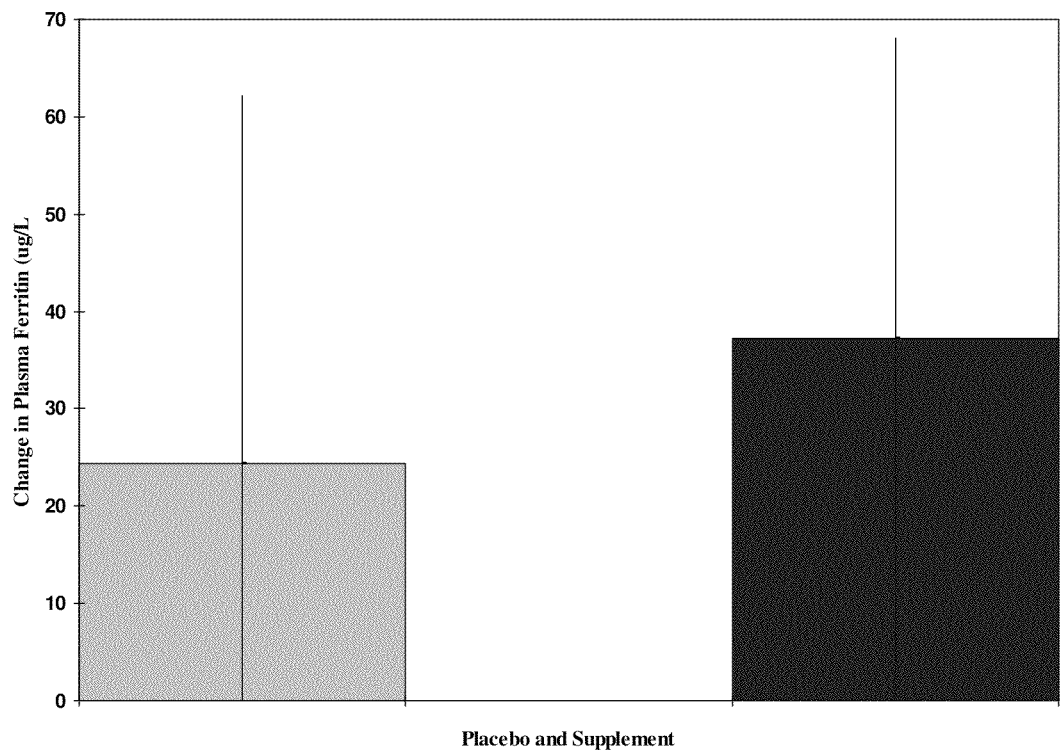
FIG. 4. The average change in blood ferritin levels after nutritional intervention.

These were done primarily to gauge changes in mineral status. Plasma ferritin tended to increase with the Test Formula II treatment and not with the other two treatments, but the increase was not significant by unpaired t-test of placebo change versus Test Formula II change. The plasma ferritin change in values for Placebo and Test Formula II are given in FIG. 3.

For zinc, plasma zinc did not change for any group, but activity of the plasma zinc enzyme 5'-nucleotidase, a more sensitive indicator of zinc status, did increase significantly in both the Test Formula I and Test Formula II groups. Although the increase was not a large percentage, this parameter can be indicative of bigger changes occurring in tissues.

|  | Placebo | Test Formula I | Test Formula II |
| --- | --- | --- | --- |
| 5'-nucleotidase-Pre | 5.3 ± 0.6 | 5.5 ± 1.2 | 5.1 ± 1.0 |
| 5'-nucleotidase-Post | 5.6 ± 0.8 | 5.8 ± 1.4* | 5.4 ± 1.1* |

Results are Units/L ± SD
*p < 0.01 paired t-test

For copper, ceruloplasmin activity was not changed by any of the treatments.

Example 2

Formulations

Any inert excipient that is commonly used as a carrier or diluent may be used in the formulations of the present invention, such as for example, a gum, a starch, a sugar, a cellulosic material, an acrylate, or mixtures thereof. The compositions may further comprise a disintegrating agent (e.g., croscarmellose sodium) and a lubricant (e.g., magnesium stearate), and in addition may comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

The nutraceutical compositions can be administered orally, and are thus formulated in a form suitable for oral administration, i.e., as a solid or a liquid preparation. Suitable solid oral formulations include tablets, capsules, pills, granules, pellets and the like. Suitable liquid oral formulations include solutions, suspensions, dispersions, emulsions, oils and the like.

As used herein, "acceptable carrier" is intended to include any and all solvents, dispersion media, coatings, antibacterial and antifungal agents, isotonic and absorption delaying agents, and the like, compatible with nutraceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for nutraceutically active substances is well known in the art. Except insofar as any conventional media or agent is incompatible with the active compound, use thereof in the compositions is contemplated. Supplementary active compounds can also be incorporated into the compositions.

Non-limiting examples of solid carriers/diluents include, but are not limited to, a gum, a starch (e.g., corn starch, pregelatinized starch), a sugar (e.g., lactose, mannitol, sucrose, dextrose), a cellulosic material (e.g., microcrystalline cellulose), an acrylate (e.g., polymethylacrylate), calcium carbonate, magnesium oxide, talc, or mixtures thereof.

Non-limiting examples of liquid formulations, nutraceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCl, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol), a glidant (e.g., colloidal silicon dioxide), anti-oxidants (e.g., ascorbic acid, sodium metabisulfite, butylated hydroxyanisole), stabilizers (e.g., hydroxypropyl cellulose, hyroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flow-aids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In certain embodiments, the active compounds can be prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as nutraceutically acceptable carriers. These can be prepared according to methods known to those skilled in the art.

It is especially advantageous to formulate oral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required nutraceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

The nutraceutical compositions can be included in a container, pack, or dispenser together with instructions for administration. For example, the compounds may be administered intravenously on the first day of administration, with oral administration on the second day and all consecutive days thereafter. The compounds of the present invention may be administered for the purpose of preventing disease progression or stabilizing tumor growth.

The preparation of nutraceutical compositions that contain an active component is well understood in the art, for example, by mixing, granulating, or tablet-forming processes. The active therapeutic ingredient is often mixed with excipients that are nutraceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound or formulation administered to the patient is less than an amount that would cause toxicity in the patient. In the certain embodiments, the amount of the compound that is administered to the patient is less than the amount that causes a concentration of the compound in the patient's plasma to equal or exceed the toxic level of the compound.

What is claimed is:
1. A nutritional supplement, comprising L-carnitine; phosphatidylserine; ferrous glycinate, copper glycinate; and zinc glycinate.
2. A nutritional supplement of claim 1, comprising:
0.5 g to 5 g L-carnitine; and
300 mg to 1.5 g phosphatidylserine;
ferrous glycinate, wherein the ferrous glycinate includes 10 mg to 75 mg iron;
copper glycinate, wherein the copper glycinate includes 0.5 to 3 mg copper; and
zinc glycinate, wherein the zinc glycinate includes 8 mg to 17 mg zinc,
wherein the supplement is apportioned amongst at least two doses.
3. A nutritional supplement of claim 1, comprising:
0.5 g to 2.5 g L-carnitine tartrate;
300 mg to 700 g to phosphatidylserine;
ferrous glycinate, wherein the ferrous glycinate includes 25 mg to 50 mg iron;
copper glycinate, wherein the copper glycinate includes 1.5 mg to 3 mg copper; and
zinc glycinate, wherein the zinc glycinate includes 13 mg to 16 mg zinc,
wherein the supplement is apportioned amongst at least two doses.
4. A multivitamin formulation, comprising:
approximately 1 g L-carnitine tartrate;
approximately 400 mg phosphatidylserine;
ferrous glycinate, wherein the ferrous glycinate includes approximately 36 mg iron;
copper glycinate, wherein the copper glycinate includes approximately 2 mg copper; and
zinc glycinate, wherein the zinc glycinate includes approximately 15 mg zinc,
wherein the formulation is apportioned amongst at least two doses.
5. A nutritional supplement of claim 1, wherein the supplement further comprises one or more composition selected from the group consisting of: protein; carbohydrate; fiber; fat; electrolyte; stimulant; vitamin; mineral; herb; polymer; water; artificial sweetener; artificial fat; and pharmoactive molecule.
6. A nutritional supplement of claim 1, which is optimized for a mammal selected from the group consisting of: mouse; rat; bovine; horse; swine; dog; cat; and human.
7. A nutritional supplement of claim 1, which is optimized for a female human.
8. A nutritional supplement of claim 1, wherein the supplement is in a form selected from the group consisting of: liquid; gel; solid; tablet; capsule; crystals; and powder.
9. A nutritional supplement of claim 1, wherein the supplement is in a form selected from the group consisting of: multivitamin; drink; bar; gel; powdered drink mix; concentrated liquid drink mix; gel drink mix; and, crystalline food.
10. A nutritional supplement of claim 1, wherein the supplement is a liquid selected from the group consisting of: water; orange juice; apple juice; grape juice; mixed juice; cranberry juice; pomegranate juice; cow's milk; goat's milk; sheep's milk; nut extract; soy extract; grain extract; carbonated beverage; alcoholic beverage; and, flavored beverage.
11. A nutritional supplement of claim 1, wherein the supplement is a food selected from the group consisting of: dairy product; ready-to-eat cereal; cookie; cake; cracker; pretzel; honey; and bar.
12. A nutritional supplement of claim 1, wherein one or more of the ingredients is formulated for a quality selected from the group consisting of: liquid dispersement resistance or enhancement; colloid formation resistance or enhancement; heat stability; powdering resistance or enhancement; dissolving resistance or enhancement; bulk formation or reduction; maillard reaction resistance or enhancement; bitterness resistance; flavor enhancement; appearance enhancement; processing enhancement; and, process expense reduction.
13. A nutritional supplement of claim 1, wherein the L-carnitine is L-carnitine tartrate.
14. A nutritional supplement of claim 1, wherein ferrous glycinate, copper glycinate and zinc glycinate is in an encapsulated, micellar form.
15. A method for measuring the exercise performance capacity in a human, comprising measuring exercise performance capacity pre-administration of the nutritional supplement of claim 1, administering the nutritional supplement of claim 1 and measuring exercise performance capacity post-administration of the nutritional supplement of claim 1.
16. A method of claim 15, wherein the human is a female human selected from the group consisting of: adult woman; and adolescent girl.
17. A method of claim 15, wherein the human is a female human competitive athlete who trains for a sport selected from the group consisting of: cross-country running; soccer; softball; volleyball; basketball; golf; track; swimming; dance; cheerleading; and triathlon.

18. A method of claim 15, wherein the supplement is administered via 1-10 servings per day.

19. A method of claim 15, wherein the supplement is administered via 4-8 servings per day.

20. A method of claim 15, wherein the supplement is administered via 6 servings per day, three times a day, via capsule or tablet.

\* \* \* \* \*